United States Patent [19]

Kopp et al.

[11] Patent Number: 4,734,532
[45] Date of Patent: Mar. 29, 1988

[54] PROCESS FOR THE PREPARATION OF 4,4'-DINITRODIBENZYLS

[75] Inventors: Richard Kopp, Cologne; Gerhard Grögler; Klaus König, both of Leverkusen; Manfred Schmidt, Dormagen, all of Fed. Rep. of Germany

[73] Assignee: Bayer Aktiengesellschaft, Leverkusen, Fed. Rep. of Germany

[21] Appl. No.: 871,018

[22] Filed: Jun. 4, 1986

[30] Foreign Application Priority Data

Jun. 28, 1985 [DE] Fed. Rep. of Germany ....... 3523204

[51] Int. Cl.$^4$ .............................................. C07C 79/10
[52] U.S. Cl. .................................... 568/931; 568/928
[58] Field of Search ............... 568/931, 928, 939, 940; 204/157.83

[56] References Cited

U.S. PATENT DOCUMENTS

| 3,716,590 | 2/1973 | Caraculacu et al. | 568/931 |
| 4,245,129 | 1/1981 | Gilbert | 568/931 |
| 4,247,724 | 1/1981 | Gilbert | 568/931 |

FOREIGN PATENT DOCUMENTS 2051167 10/1970 Fed. Rep. of Germany ...... 568/931

*Primary Examiner*—John F. Terapane
*Assistant Examiner*—Susan Wolffe
*Attorney, Agent, or Firm*—Sprung Horn Kramer & Woods

[57] ABSTRACT

4,4'-dinitrodibenzyls are prepared by reaction of 4-nitrotoluenes, in the presence of an organic solvent and/or diluent, with an alkali metal-alcoholate and/or an alkaline earth metal alcoholate, and subsequent treatment of the reaction mixture with an aqueous solution of hypohalous acids and/or their salts or with chlorine, bromine or an aqueous solution of hydrogen peroxide and/or its salts, or with organic or inorganic peracids and/or their salts.

17 Claims, No Drawings

PROCESS FOR THE PREPARATION OF 4,4'-DINITRODIBENZYLS

BACKGROUND OF THE INVENTION

The present invention relates to a process for the preparation of 4,4'-dinitrodibenzyls from 4-nitrotoluenes by oxidative dimerization.

The preparation of 4,4'-dinitrodibenzyl from 4-nitrotoluene by oxidative dimerization with atmospheric oxygen in strongly alkaline solution has been disclosed and is described in, for example, *Chem. Berichte*, 26, 2232 (1893), *J. Chem. Soc.*, 91, 2079 (1907), *J. Amer. Chem. Soc.*, 75, 1325 (1953) and *Org. Synth. Coll.*, Vol. IV, 367 (1963). The mechanism of the said reaction has also been thoroughly investigated (see, for example, *J. Amer. Chem. Soc.*, 75, 3265 (1955), Abstr. of Papers, 135th Meeting Amer. Chem. Soc., April 5-14, 1960, pages 6-25; *Monatsh. Chem.*, 34, 1011 (1913), *J. Amer. Chem.*, *Soc.* 84, 4153 (1962) and *J. Amer. Chem. Soc.*, 88, 5491 (1966)).

An improved process for the preparation of 4,4'-dinitrodibenzyl from 4-nitrotoluene by oxidative dimerization with oxygen in alkaline solution is described in *J. Org. Chem.* 26, 4162 (1961) and in U.S. Pat. No. 2,965,681. These processes are carried out in the presence of certain amines or ethers.

Furthermore, DE-OS (German Published Specification) No. 2,051,167 discloses a process for the preparation of 4,4'-dinitrodibenzyl in which the oxidative dimerization is carried out with air or oxygen in methanolic or ethanolic NaOH or KOH solution, and in which a special reactor is used.

Oxidative dimerization in strongly alkaline solution using air or oxygen is the only process which has hitherto been disclosed for the preparation of industrial amounts of dinitrodibenzyl. Other methods, such as the reaction of 4-nitrotoluene with 0.5 mol of diethyl oxalate and 1 mol of sodium methylate (*Chem. Ber.*, 30, 1053 (1897), *Ann. Chem.*, 436, 56 (1924)), the reaction of 4-nitrobenzyl chloride with alkaline stannate solution (German Pat. No. 39,381), the action of mercury oxide on α,α-bis[4-nitrobenzyl]hydrazine dissolved in chloroform (*Chem. Ber.*, 33, 2710 (1910)) or the nitration of dibenzyl (*J. Amer. Chem.*, 52, 5040 (1930), *J. Chem. Soc. Jap. Ind. Chem. Sect.*, 61, 469 (1958)), have likewise been disclosed but have not hitherto aroused industrial interest.

The abovementioned processes for the preparation of 4,4'-dinitrodibenzyl by oxidation of 4-nitrotoluene with air or oxygen are, however, associated with considerable disadvantages. The amounts of bases used for the preparation of the reactive intermediate from 4-nitrotoluene are at least 4 to 5 mol, 10 mol of base in fact being preferred, per mol of 4-nitrotoluene. Furthermore, the reaction is normally carried out at very low concentrations of nitrotoluene (about 5% strength solutions) since otherwise the reaction times become too long. Nevertheless, even under these conditions reaction times of about 6 to 8 hours are necessary for the air oxidation. However, this means that the space/time yields are poor, which is at the expense of the economics of the processes mentioned. Furthermore, it is necessary, in order to avoid the formation of 4,4'-dinitrostilbene, to carry out the reaction at relatively low temperatures, that is to say with cooling. An additional disadvantage of the said processes is that the product results in very finely divided form and thus the filtration of the product is associated with great industrial difficulties. In addition, large amounts of intensely colored filtrates are produced, and their working up likewise demands considerable industrial effort.

SUMMARY OF THE INVENTION

A process for the preparation of 4,4'-dinitrodibenzyls of the general formula

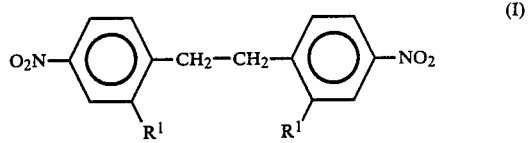

in which
R$^1$ represents hydrogen, alkyl, aryl, alkaryl, aralkyl or halogen, has now been found, which process is characterized in that 4-nitrotoluenes of the general formula

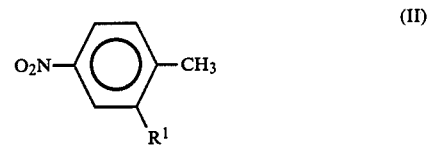

in which
R$^1$ has the abovementioned meaning, are reacted, in the presence of an organic solvent and/or diluent, with an alkali metal alcoholate and/or an alkaline earth metal alcoholate, and then the reaction mixture is treated with an aqueous solution of hypohalous acids and/or their salts, or with chlorine, bromine or an aqueous solution of hydrogen peroxide and/or its salts, or with inorganic or organic peracids and/or their salts.

DETAILED DESCRIPTION OF THE INVENTION

The alkyl radicals of the formula (I) which may be mentioned are those having 1 to 18 carbon atoms, preferably 1 to 5 carbon atoms, such as methyl, ethyl, n-propyl, iso-propyl, n-butyl, sec.-butyl, iso-butyl, tert.-butyl, pentyl, hexyl, 2-ethylhexyl, decyl, dodecyl, octadecyl and cyclohexyl, preferably methyl and ethyl; the aryl radicals are those having 6 to 20 carbon atoms, preferably 6 to 10 carbon atoms, such as phenyl, chlorophenyl, bromophenyl and naphthyl, preferably phenyl and naphthyl; the alkaryl radicals are those having 7 to 20 carbon atoms, preferably 7 to 10 carbon atoms, such as p-tolyl, m-tolyl, o-tolyl, ethylphenyl, propylphenyl and isopropylphenyl, preferably p-tolyl; the aralkyl radicals are those having 7 to 20 carbon atoms, preferably 7 to 10 carbon atoms, such as benzyl, phenethyl, 3-phenylpropyl and 2-phenylpropyl, preferably benzyl, and the halogens are F, Cl and Br, preferably Cl.

Examples of suitable starting compounds of the general formula (II) are: 4-nitrotoluene, 1,2-dimethyl-4-nitrobenzene, 2-ethyl-4-nitrotoluene, 2-propyl-4-nitrotoluene, 2-phenyl-4-nitrotoluene, 2-benzyl-4-nitrotoluene, 2-fluoro-4-nitrotoluene, 2-chloro-4-nitrotoluene and 2-bromo-4-nitrotoluene, preferably 4-nitrotoluene, 1,2-dimethyl-4-nitrobenzene, 2-ethyl-4-nitrotoluene and 2-chloro-4-nitrotoluene.

Suitable organic solvents and/or diluents are all solvents and/or diluents which have a solubility for the 4-nitrotoluene and the alcoholate base which is adequate for the reaction with 4-nitrotoluene. If aqueous solutions of oxidizing agents are used for the oxidative dimerization, then the organic solvents should have a water solubility of $\geqq 2\%$, preferably $\geqq 5\%$, particularly preferably $\geqq 10\%$. Furthermore, their solubility for the resulting dinitrodibenzyl should not be too great, since otherwise its isolation is made difficult and the oxidation reaction can very easily, especially when excess amounts of base are used, continue on to the stage of the dinitrostilbene. Likewise, a relatively low acid strength of the solvent has an advantageous effect on the course of the reaction. For this reason, the preferred organic solvents and/or diluents are alcohols, such as methanol, ethanol, propanol, iso-propanol, n-butanol, iso-butanol, sec.-butanol, tert.-butanol, tert.-amyl alcohol, ethylene glycol monomethyl ether, ethylene glycol monobutyl ether, diethylene glycol and/or diethylene glycol monomethyl ether, particularly preferably tert.-butanol, tert.-amyl alcohol, methanol, ethylene glycol monomethyl ether, ethylene glycol monobutyl ether, diethylene glycol and/or diethylene glycol monomethyl ether, and ethers, such as diethyl ether, di-isopropyl ether, dibutyl ether, tert.-butyl methyl ether, tetrahydrofuran, 1,4-dioxane and/or 1,3-dioxane and particularly preferably tert.-butyl methyl ether, tetrahydrofuran or 1,4-dioxane.

Likewise suited are optionally substituted carboxamides, such as N,N-dimethylformamide, N,N-dimethylacetamide and/or N-methylpyrrolidone. Other solvents and/or diluents which can also be used are carboxylic esters and/or ketones, such as ethyl acetate, butyl acetate, ethylene glycol monomethyl ether acetate, acetone, methyl ethyl ketone and/or cyclohexanone. Hydrocarbons, such as pentane, hexane, petroleum ether, wash benzine, benzene, toluene and/or xylene, are, because of the low water solubility, preferably used in combination with water-miscible solvents such as methanol.

Halogenated hydrocarbons can only be used if the contained halogen cannot be eliminated as hydrohalogen by bases under the reaction conditions. Examples which may be mentioned are chlorobenzene, o-dichlorobenzene, m-dichlorobenzene and chlorotoluene.

The abovementioned alcohols, particularly preferably tert.-butanol or its mixture with methanol, are preferably used for the reaction according to the invention.

The alkali metal alcoholates or alkaline earth metal alcoholates which are normally used in the process according to the invention are those which are derived from open-chain, branched or cyclic lower aliphatic alcohols having 1 to 8 carbon atoms, preferably 1 to 5 carbon atoms. These alcoholates are preferably used as corresponding alcoholic solutions. Preferably, use is made in the process according to the invention of the sodium or potassium alcoholates of the alcohol which is used as the reaction medium, such as sodium methanolate or potassium tert.-butanolate. The preparation of the alkali metal or alkaline earth metal alcoholates is known and described in, for example, *Houben-Weyl, Methoden der organischen Chemie* (Methods of Organic Chemistry), 4th edition, volume VI/2, page 1 et seq.

The oxidizing agents used in the process according to the invention are aqueous solutions of hypohalous acids and/or their salts, elementary chlorine or bromine, aqueous solutions of hydrogen peroxide and/or its salts, or inorganic or organic peracids and/or their salts. The solutions of hypohalous acids and/or their salts which are preferably used are the sodium hypochlorite solutions which are known under the trivial name Labarraque's solution, bleaching liquor or hypochlorite solution, which are obtained by electrolysis of sodium chloride solutions or by passing chlorine gas into sodium hydroxide solution, and which contain about 12.5 to 13% by weight of active chlorine.

The aqueous hydrogen peroxide solutions which are used are solutions containing from about 5 to 65% by weight of hydrogen peroxide, preferably 20 to 50% by weight of hydrogen peroxide, particularly preferably 30 to 35% by weight of hydrogen peroxide.

Examples of peracids and of their salts which may be mentioned are perborates, such as Na perborate, perchlorates, such as K perchlorate, chlorates, permanganates, peroxomono- and -dicarbonates, peroxomono- and disulphates, peroxophosphates and perbenzoic acid.

For the preparation of the dinitrodibenzyls, the corresponding nitrotoluenes are first reacted with the alcoholate in an organic solvent and/or diluent. For this purpose, one of the reactants is initially introduced, where appropriate dissolved in a portion or all of the organic solvent and/or diluent, and the other reactant, dissolved in the remainder of the organic solvent and/or diluent, is added all at once or in portions. The reaction takes place exothermically so that cooling is necessary where appropriate. It has emerged that a temperature range favorable for carrying out the reaction is from about 20° to 70° C., preferably 30° to 50° C., particularly preferably 35° to 45° C. When the temperatures are too low the reaction takes place too slowly, and when the temperatures are too high an increasing proportion of dinitrostilbene by-products is found.

In general, a molar excess of alkali metal alcoholate and/or alkaline earth metal alcoholate is used in the process according to the invention. Normally, about 1.05 to 5 mol, preferably 1.1 to 3 mol, of alkali metal alcoholate and/or alkaline earth metal alcoholate is used per mol of 4-nitrotoluene. The amount of base which is optimum in each case can readily be determined by a few preliminary tests. For example, when sodium methanolate is used as the base a molar amount which is about three times that of the 4-nitrotoluene has proved favorable; when potassium tert.-butanolate is used a smaller (about 5 to 10%) molar excess suffices. If less than molar amounts of bases are used then there is a corresponding decrease in the yield of 4,4'-dinitrodibenzyl (see Example 3). The formation of the carbanion (intense yellow coloration) and the subsequent radical stages (red-blue-violet coloration) generally takes place very rapidly so that the oxidation reaction can be carried out immediately after the reactants have been completely mixed or after only a short time has elapsed. For this purpose, the oxidizing agent is added to, or passed as gas (chlorine) into, the basic 4-nitrotoluene solution, with stirring. The treatment of the reaction mixture with oxidizing agents is preferably carried out in the same temperature range as the reaction with the base. The reaction is likewise exothermic, and cooling is necessary where appropriate.

The amount of oxidizing agent in the process according to the invention is generally 0.1 to 2.0 mol, preferably 0.5 to 1.5 mol, relative to 1 mol of the 4-nitrotoluene of formula II.

In the case of hypochlorite solution the oxidative dimerization takes place spontaneously, that is to say the reaction can be terminated and worked up immediately after addition of the hypochlorite solution is complete. In the case of hydrogen peroxide, of bromine or chlorine as the oxidizing agent, or of the other oxidizing agents, short after-reaction times of up to about ½ hour are advantageous. Because of the rapid reaction, it is also possible to carry out the overall process continuously.

After completion of the reaction the dibenzyl product is isolated by customary processes. The isolation is preferably carried out by addition of water and filtration of the precipitated product with suction. However, because of the high yields, it is also possible first to evaporate the reaction mixture almost to dryness and then to suspend and wash the product several times with water. The drying is carried out by customary standard processes, preferably in a vacuum drying oven at temperatures of about 50° C. and under 20 to 100 mbar. The working up of the reaction mixture is facilitated if it is neutralized by addition of acids, such as aqueous hydrochloric acid or sulphuric acid, before the addition of water.

Compared with the oxidative dimerization in alkali metal hydroxide/methanol mixtures hitherto known, the process according to the invention is distinguished by, on the one hand, a lower excess of base being necessary for the preparation of the reactive intermediate and, on the other hand, it is possible to use higher concentrations of charge stock. Furthermore, the oxidation reaction with an aqueous hypochlorite solution or with chlorine, bromine or an aqueous solution of hydrogen peroxide, or the other oxidizing agents which have been mentioned, takes place very rapidly so that, overall, considerably higher space-time yields can be achieved than by the processes of the state of the art.

It is particularly surprising that such high yields of 4,4'-dinitrodibenzyls can be achieved in the process according to the invention since, according to *J. Chem. Soc.*, 91, page 2079 (1907), oxidation of 4-nitrotoluene with hypochlorite solutions is regarded as being impossible.

The examples which follow are intended to illustrate the process according to the invention, but without restricting it to these examples.

4,4'-Dinitrodibenzyls and 4,4'-diaminodibenzyls are useful as hardener for epoxy- and isocyanate-prepolymers and for the preparation as isocyanates.

EXAMPLE 1

68.5 g (0.5 mol) of 4-nitrotoluene in 200 ml of tert.-butanol are initially introduced at 40° C.

67.2 g (0.6 mol) of potassium tert.-butanolate, dissolved in 400 ml of tert.-butanol, are added within 5 min at 40° C., with stirring (immediate color change to intense yellow, orange, red and violet). The mixture is then stirred at 40° C. for 10 minutes.

(a) 19.5 g (0.275 mol) of chlorine gas are passed in within 1 hour, or
(b) 48 g (0.30 mol) of bromine are added dropwise within 20 minutes, or
(c) 26.7 g (0.275 mol) of 35% aqueous hydrogen peroxide solution are added dropwise within 15 minutes, or
(d) 150 g (0.55 mol Cl) of hypochloride solution containing 13% active chlorine, or a solution of (e) 67.6 g (0.25 mol) of potassium persulphate ($K_2S_2O_8$) in 600 ml water at 40° C., is added dropwise within 15 minutes. The mixture is then stirred at 40° C. for 30 minutes.

After addition of 500 ml of water, the resulting solid is filtered off with suction, washed to neutrality with water, and dried at 50° C.

| No. | a | b | c | d | e |
|---|---|---|---|---|---|
| Yield | 65.5 g | 60.9 g | 63.87 g | 55.6 g | 56.6 g |
| Melting point | 174 to 225° C. | 174 to 225° C. | 174 to 225° C. | 174 to 225° C. | 172 to 225° C. |

Relative composition by HPLC:

| | | | | | |
|---|---|---|---|---|---|
| 4-Nitrotoluene | 1.6% | 1.6% | 1.8% | 2.9% | 2.4 |
| Dinitrodibenzyl | 84.2% | 91.3% | 87.5% | 90.0% | 91.5 |
| Dinitrostilbene | 10.5% | 4.2% | 7.7% | 4.9% | 0.6 |

Example 1 shows the fundamental suitability of the oxidizing agents chlorine, bromine, hypochlorite solution, hydrogen peroxide/water and K persulphate for the oxidative dimerization of 4-nitrotoluene, and demonstrates the high rates of reaction with the oxidizing agents and bases according to the invention.

Comparison experiment

For comparison, an experiment in which, after the preliminary reaction with potassium tert.-butanolate, air was passed through the reaction mixture at 40° C. for 5 hours was carried out. The working up was carried out as described in Example 1a to e.

Yield: 67.7 g
Melting point: 230° to >280° C.
Relative composition by HPLC:

| | |
|---|---|
| 4-Nitrotoluene | |
| Dinitrodibenzyl | 37.7% |
| Dinitrostilbene | 59.0% |

The comparison experiment shows that although the concentration of starting material in the reaction solution can be increased when alcoholates are used as bases, the reaction times necessary for oxidation with atmospheric oxygen are considerably longer than with the oxidizing agents according to the invention. In addition, it emerges that, at the same temperature, the tendency for the formation of the dinitrostilbene derivative is considerably greater when atmospheric oxygen is used as the oxidizing agent, that is to say the reaction has to be carried out at lower temperatures (with cooling).

EXAMPLE 2

411 g (3 mol) of 4-nitrotoluene in 1500 ml of tert.-butanol at 40° C. are initially introduced.

1620 g (9 mol) of a 30% strength solution of sodium methanolate in methanol are added within 20 minutes, while stirring, the temperature being maintained at 35°–40° C. by cooling. 15 min after addition is complete, 154 g (1.59 mol) of a 35% strength hydrogen peroxide solution are added dropwise within 30 minutes, while stirring, the temperature being maintained at 40° C. by slight cooling. A yellow-orange precipitate gradually separates out. After addition is complete, the mixture is stirred at 40° C. for 1 hour. The reaction mixture is cooled to about 20° C., neutralized (pH=7) with halfconcentrated hydrochloric acid, and 1000 ml of water are added. The precipitated product is filtered off with suction, washed with water and dried.

Yield: 340.3 g
Melting point: 165° to 228° C.
Relative composition by HPLC:
4-Nitrotoluene: 3.0%
Dinitrodibenzyl: 82.3%
Dinitrostilbene: 5.3%

A tert.-butanol/methanol mixture is used as the reaction medium in this example. The example demonstrates that even larger batches can be carried out without difficulty (cooling).

EXAMPLE 3

68.5 g (0.5 mol) of 4-nitrotoluene are initially introduced at 40° C. While stirring, a solution of 33.6 g (0.3 mol) of potassium tert.-butanolate in 650 ml of tert.-butanol at 40° C. is added within 2 minutes. The mixture is then stirred at 40° C. for 10 minutes (a) 26.7 g (0.275 mol) of a 35% strength hydrogen peroxide solution or
(b) 150 g of hypochlorite solution containing 13% active chlorine are added dropwise, while stirring at 40° C., within 15 minutes. This mixture is then stirred at 40° C. for 30 min, cooled to 20° C., water is added, and the solid is filtered off with suction, washed to neutrality with water, and dried.

Yield: 37.29 g 38.1 g
Melting point: 165° to 225° C. 163° to 225° C.
Relative composition by HPLC:

| 4-Nitrotoluene | 2.6% | 2.9% |
|---|---|---|
| Dinitrodibenzyl | 91.5% | 94.2% |
| Dinitrostilbene | 1.4% | 1.3% |

Example 3 shows that when the oxidizing agents according to the invention are used the yield depends on the amount of base used (compare with Example 1c and 1d).

EXAMPLE 4

68.5 g (0.5 mol) of 4-nitrotoluene are initially introduced at 40° C. While stirring, a mixture of 67.2 g (0.6 mol) of potassium tert.-butanolate in 400 ml of tert.-butanol at 40° C. is added within a few minutes. Immediately thereafter, 150 g of hypochlorite solution containing 13% active chlorine is added drop-wise, while stirring at 40° C., within 15 minutes. A yellow-oragne precipitate immediately separates out. The mixture is then stirred at 40° C. for 30 minutes, cooled to 20° C., 500 ml of water added, and the product is filtered off with suction, washed to neutrality with water, and dried.

Yield: 53.0 g
Melting point: 160° to 215° C.
Relative composition by HPLC:
4-Nitrotoluene: 2.5%
Dinitrodibenzyl: 88.4%
Dinitrostilbene: 2.7%

Example 4 shows that the reaction of the base with the 4-nitrotoluene takes place very rapidly so that the oxidation reaction, which likewise takes place instantaneously, can be carried out virtually immediately thereafter, which is very important for a continuous procedure.

EXAMPLE 5

Example 5 is carried out in the same manner as Example 1d but with the following modification:

After the addition of the hypochlorite solution and stirring at 40° C. for 30 minutes, the entire mixture is evaporated almost to dryness in a rotary evaporator at a bath temperature of 40° C., a clear mixture of water and tert.-butanol distilling over. The residue is taken up in hot water, and the solid is filtered off with suction, washed 3 times with hot water and dried.

Yield: 65.6 g
Melting point: 170° to 223° C.
Relative composition by HPLC:
4-Nitrotoluene: 7.6%
Dinitrodibenzyl: 78.4%
Dinitrostilbene: 9.4%

EXAMPLE 6

Example 6 is carried out in the same manner as Example 1c but with the following modification:

After the addition of the hydrogen peroxide solution and stirring at 40° C. for 30 minutes, the entire mixture is evaporated almost to dryness in a rotary evaporator at a bath temperature of 40° C., a clear mixture of water and tert.-butanol distilling over. The residue is taken up in hot water, and the solid is filtered off with suction, washed 3 times with hot water and dried.

Yield: 66.8 g
Melting point: 172° to 223° C.
Relative composition by HPLC:
4-Nitrotoluene: 1.4%
Dinitrodibenzyl: 86.6%
Dinitrostilbene: 9.3%

Example 5 and 6 show that the yields can be considerably increased if part of the reaction medium is removed before the working up, that is to say losses of yield occur owing to the solubility of the products in the reaction medium.

EXAMPLE 7

Variations in temperature 68.5 g (0.5 mol) of 4-nitrotoluene are initially introduced at a temperature of X° C., and 67.2 g (0.6 mol) of potassium tert.-butanolate in 650 ml of tert.-butanol are added in about 10 minutes, while stirring, the temperature being maintained at X° C. After addition is complete, the mixture is stirred for 10 minutes. While stirring, within about 15 minutes 26.7 g (0.275 mol) of a 35% strength hydrogen peroxide solution are added, the temperature being maintained at Y° C. The mixture is then stirred at Y° C. for 30 minutes. The reaction mixture is cooled to about 20° C., 500 ml of water is added, and the precipitate is filtered off with suction, washed to neutrality with water and dried.

| | a | b | c |
|---|---|---|---|
| X | 40° C. | 30° C. | 55° C. |
| Y | 55° C. | 40° C. | 40° C. |
| Yield | 62.5 g | 61.6 g | 65.0 g |
| Melting point | 188 to 245° C. | 178 to 210° C. | 165 to 228° C. |

Relative composition by HPLC:

| 4-Nitrotoluene | 0.8% | 1.2% | 2.1% |
|---|---|---|---|
| Dinitrodibenzyl | 78.2% | 90.8% | 86.4% |

|  | -continued |  |  |
|---|---|---|---|
| Dinitrostilbene | 16.4% | 5.5% | 7.5% |

The effect on the production composition of the reaction temperature of the base reaction and of the oxidation reaction is demonstrated in this example. A lower temperature for the base reaction leads to higher proportions of dinitrodibenzyl in the final product, at the cost of a reduced yield (compare Example 1c), higher temperatures for the oxidation reaction lead to an increase in the proportion of dinitrostilbene in the final product.

EXAMPLE 8

68.2 g (0.6 mol) of potassium tert.-butanolate are dissolved in 650 ml of tert.-butanol, the temperature rising to 38° C. The mixture is cooled to 23° C. and, while stirring, 68.5 g (0.5 mol) of powdered 4-nitrotoluene are added all at once, the temperature rising to 30° C. The mixture is then stirred for 10 minutes without further heating or cooling. 150 g of hypochlorite solution containing 13% by weight of active chlorine are added dropwise, while stirring without cooling, within 15 minutes, the temperature rising to 44° C. After stirring for 30 minutes, 500 ml of water are added, and the precipitated product is filtered off with suction, washed to neutrality with water and dried.

Yield: 44.4 g
Melting point: 168° to 175° C.
Relative composition by HPLC:
4-Nitrotoluene: 2.5%
Dinitrodibenzyl: 93.0%
Dinitrostilbene: —

Example 8 shows that it is possible, by suitably controlling the reaction, to reduce the proportion of dinitrostilbene in the final product to an amount which is no longer detectable by chromatography.

EXAMPLE 9

27.4 g (0.2 mol) of 4-nitrotoluene are initially introduced at 40° C., and 28.0 g (0.25 mol) of potassium tert.-butanolate dissolved or dispersed in 250 ml of a solvent are added, while stirring at 40° C. The mixture is then stirred at 40° C. for 10 minutes. Then, while stirring, 60 g of hypochlorite solution containing 13% active chlorine are added within 15 minutes. After stirring at 40° for a further 30 minutes, 200 ml of water are added, and the precipitated solid is filtered off with suction, washed to neutrality with water and dried at 50° C.

|  | a | b | c |
|---|---|---|---|
| Solvent | Tetrahydrofuran | N,N—Dimethylformamide | tert.-Butyl methyl ether |
| Yield | 12.0 g | 25.4 g | 19.8 g |
| Melting point | 165 to 228° C. | 230 to 275° C. | 170 to 267° C. |

Relative composition by HPLC:

|  | | | |
|---|---|---|---|
| 4-Nitrotoluene | 3.8% | 6.0% | 3.4% |
| Dinitrodebenzyl | 91.4% | 31.3% | 89.8% |
| Dinitrostilbene | 1.6% | 57.5% | 2.6% |

Example 9 shows the effect of the solvent on the oxidative dimerization of 4-nitrotoluene. Solvents with low polarity and thus lower solubility for the alcoholate (Example a and c) lead to low yields which, however, have a high proportion of dinitrobenzyl.

Solvents with high solubility for the base, starting material and final product lead, in high yield, to products which have a considerable proportion of dinitrostilbene (Example b).

EXAMPLE 10

75.5 g (0.5 mol) of 1,2-dimethyl-4-nitrobenzene, dissolved in 150 ml of tert.-butanol are added dropwise, within about 5 minutes, to a mixture of 67.2 g (0.6 mol) of potassium tert.-butanolate in 150 ml of tert.-butanol at 40° C., with stirring. The mixture is then stirred for 10 minutes and subsequently, while stirring at 40° C., 150 g of hypochlorite solution containing 13% active chlorine are added within 15 minutes. After 30 minutes, 500 ml of water are added, and the precipitated product is filtered off with suction, washed to neutrality with water and dried.

Yield: 67.0 g
Melting point: 198° to 212° C.
Relative composition by HPLC:
1,2-Dimethyl-4-nitrobenzene: 5.5%
Dinitrodibenzyl: 92.2%
Dinitrostilbene: —

The oxidative dimerization of the somewhat less activated compound 1,2-dimethyl-4-nitrobenzene takes place at least as well as for 4-nitrotoluene. Virtually the only product is the corresponding dinitrodibenzyl.

EXAMPLE 11

85.75 g (0.5 mol) of 2-chloro-4-nitrotoluene in 100 ml of tert.-butanol are initially introduced at 40° C. While stirring, a mixture of 67.2 g (0.6 mol) of potassium tert.-butanolate and 300 ml of tert.-butanol is added dropwise within 5 minutes, the temperature being maintained at 40° C. The mixture is stirred for 10 minutes after addition is complete. Then 150 g of hypochlorite solution containing 13% of active chlorine are added dropwise, while stirring, within 15 minutes, and the temperature is maintained at 40° C. during this. After stirring at 40° C. for a further 30 minutes, the mixture is cooled to 20° C. and 500 ml of water are added. The precipitate is filtered off with suction, washed to neutrality with water, and dried in a drying oven.

Yield: 85.5 g
Melting point: 230° to 265° C.
Relative composition by HPCL:
2-Chloro-4-nitrotoluene: 11.3%
Dinitrodibenzyl: 55.0%
Dinitrostilbene: 23.2%

2-Chloro-4-nitrotoluene is more highly activated for the oxidative dimerization than is 4-nitrotoluene electronwithdrawing effect of the Cl atom). For this reason, a relatively large amount of the corresponding dinitrostilbene again occurs as by-product.

EXAMPLE 12

200 g of a product which was obtained according to Example 1b and which had the following reactive composition by HPLC: 1.7% 4-nitrotoluene, 92.4% dinitrodibenzyl and 5.9% dinitrostilbene were suspended in 1800 ml of methanol, and 30 g of Raney nickel were added, and the mixture was hydrogenated under a pressure of 40 to 60 bar of $H_2$ at 60° to 80° C. The resulting mixture is filtered hot to remove Raney nickel, evaporated to about ⅓ to ½ of its original volume, and 1 liter of water is added. A nacreous precipitate separates out, and is filtered off with suction, washed with water and dried. It is 4,4'-diaminidibenzyl, which has a purity of ≧98% by HPLC.

Yield: 132.7 g (=85.1% of theory based on the total weight of the starting material)

Melting point: 126° to 130° C.

It will be appreciated that the instant specification and claims are set forth by way of illustration and not limitation, and that various modifications and changes may be made without departing from the spirit and scope of the present invention.

We claim:

1. A process for the preparation of 4,4'-dinitrodibenzyls of the formula

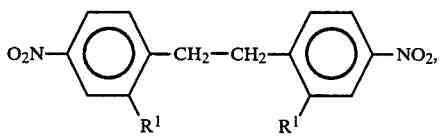

in which

R¹ represents hydrogen, alkyl, aryl, alkaryl, aralkyl or halogen, comprising reacting a 4-nitrotoluene of the general formula

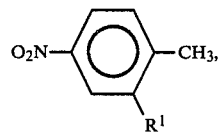

in which

R¹ has the abovementioned meaning, in the presence of an organic solvent and/or diluent, with an alkali metal-alcoholate and/or an alkaline earth metal alcoholate, and then treating the resultant reaction mixture with an oxidizing agent selected from the group consisting of an aqueous solution of a hypohalous acid, an aqueous solution of a hypohalous salt, chlorine, bromine, an aqueous solution of hydrogen peroxide, an aqueous solution of a salt of hydrogen peroxide, an inorganic peracid, an organic peracid, a salt of an inorganic peracid and a salt of an organic peracid.

2. A process according to claim 1, wherein R¹ is selected from the group consisting of hydrogen, a C₁ to C₁₈ alkyl radical, a C₆ to C₂₀ aryl radical, a C₇ to C₂₀ alkaryl radical, a C₇ to C₂₀ aralkyl radical, fluorine, chlorine and bromine.

3. A process according to claim 1, wherein said alkyl is selected from the group consisting of methyl, ethyl, n-propyl, iso-propyl, n-butyl, sec.-butyl, iso-butyl, tert.-butyl, pentyl, hexyl, 2-ethylhexyl, decyl, dodecyl, octadecyl and cyclohexyl.

4. A process according to claim 1, wherein said aryl is selected from the group consisting of phenyl, chlorophenyl, bromophenyl and naphthyl.

5. A process according to claim 1, wherein said alkaryl is selected from the group consisting of p-tolyl, m-tolyl, o-tolyl, ethylphenyl, propylphenyl and isopropylphenyl.

6. A process according to claim 1, wherein said aralkyl is selected from the group consisting of benzyl, phenethyl, 3-phenylpropyl and 2-phenylpropyl.

7. A process according to claim 1, wherein said 4-nitrotoluene is selected from the group consisting of 4-nitrotoluene, 1,2-dimethyl-4-nitrobenzene, 2-ethyl-4-nitrotoluene, 2-propyl-4-nitrotoluene, 2-phenyl-4-nitrotoluene, 2-benzyl-4-nitrotoluene, 2-fluoro-4-nitrotoluene, 2-chloro-4-nitrotoluene and 2-bromo-4-nitrotoluene.

8. A process according to claim 1, wherein said organic solvents and/or diluents are selected from the group consisting of alcohols, carboxamides, carboxylic esters, ketones esters, unhalogenated hydrocarbons and halogenated hydrocarbons.

9. A process according to claim 1, wherein said organic solvent and/or diluent is tert.-butanol mixed with methanol.

10. A process according to claim 1, wherein the alkali metal-alcoholate and/or alkaline earth metal alcoholates are those derived from open chain, branched or cyclic lower aliphatic alcohols having 1 to 8 carbon atoms.

11. A process according to claim 1, wherein the alkali metal alcoholate and/or alkaline earth metal alcoholate is sodium methanolate or potassium tert.-butanolate.

12. A process according to claim 1, wherein the hypohalous acid is a sodium hypochlorite solution which has a content of 12.5 to 13% by weight of active chlorine.

13. A process according to claim 1, wherein a molar excess of alkali metal alcoholate and/or alkaline earth metal alcoholate is used.

14. A process according to claim 1, wherein 1.05 to 5 moles of alkali metal alcoholate and/or alkaline metal alcoholate are used per mole of the 4-nitrotoluene.

15. A process according to claim 1, wherein 0.1 to 2.0 moles of oxidizing agent are used per mole of the 4-nitrotoluene.

16. A process according to claim 1, wherein the reaction is conducted at a temperature of 20° C. to 70° C.

17. A process according to claim 1, wherein the organic solvent and/or diluent is selected from the group consisting of methanol, ethanol, propanol, iso-propanol, n-butanol, iso-butanol, sec.-butanol, tert.-butanol, tert.-amyl alcohol, ethylene glycol monomethyl ether, ethylene glycol monobutyl ether, diethylene glycol, diethylene glycol monomethyl ethyl, diethyl ether, di-isopropyl ether, dibutyl ether, tert.-butyl methyl ether, tetrahydrofuran, 1,4,-dioxane, 1,3-dioxane, N,N-dimethylformamide, N,N-dimethylacetamide, N-methylpyrrolidone, ethyl acetate, butyl acetate, ethylene glycol monomethyl ether acetate, acetone, methyl ethyl ketone, cyclohexanone, pentane, hexane, petroleum ether, wash benzine, benzene, toluene, xylene, chlorobenzene, o-dichlorobenzene, m-dichlorobenzene and chlorotoluene.

* * * * *